United States Patent
Grandbois et al.

(10) Patent No.: US 9,440,923 B2
(45) Date of Patent: Sep. 13, 2016

(54) PROCESS FOR THE PREPARATION OF 4,5,6-TRICHLOROPICOLINIC ACID

(71) Applicant: Dow AgroSciences LLC, Indianapolis, IN (US)

(72) Inventors: Matthew L. Grandbois, Midland, MI (US); David S. Laitar, Midland, MI (US); James M. Renga, Spokane, WA (US); Gregory T. Whiteker, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/818,389

(22) Filed: Aug. 5, 2015

(65) Prior Publication Data

US 2016/0039760 A1  Feb. 11, 2016

Related U.S. Application Data

(60) Provisional application No. 62/033,970, filed on Aug. 6, 2014.

(51) Int. Cl.
*C07D 213/79* (2006.01)
*C07D 213/803* (2006.01)
*B01J 31/18* (2006.01)

(52) U.S. Cl.
CPC ........ *C07D 213/803* (2013.01); *B01J 31/1815* (2013.01); *B01J 2531/847* (2013.01)

(58) Field of Classification Search
None
See application file for complete search history.

(56) References Cited

U.S. PATENT DOCUMENTS 6,784,137 B2   8/2004   Balko et al.
8,609,855 B2   12/2013  Whiteker et al.

*Primary Examiner* — Zinna Northington Davis
(74) *Attorney, Agent, or Firm* — Michael R. Asam

(57) ABSTRACT

4,5,6-Trichloropicolinic acid is prepared by selectively dechlorinating 3,4,5,6-tetrachloropicolinic acid with zinc and a catalyst prepared from a nickel compound and a bidentate ligand in a polar solvent.

13 Claims, No Drawings

PROCESS FOR THE PREPARATION OF 4,5,6-TRICHLOROPICOLINIC ACID

CROSS REFERENCE TO RELATED APPLICATIONS

This application claims the benefit of U.S. Provisional Patent Application Ser. No. 62/033,970 filed Aug. 6, 2014, which is expressly incorporated by reference herein.

BACKGROUND

U.S. Pat. No. 8,609,855 B2 describes the preparation of 4-amino-5-fluoro-3-halo-6-(substituted)picolinates from 4,5,6-trichloropicolinates by a series of steps involving fluorine exchange, amination, halogen exchange, halogenation and transition metal assisted coupling. The 4,5,6-trichloropicolinate starting materials are typically prepared by the chlorination of 5,6-dichloropyridine-2-carboxylate-N-oxide; see, for example, Example 3 in U.S. Pat. No. 6,784,137 B2. It would be desirable to conveniently prepare the 4,5,6-trichloropicolinate starting materials from a more readily available source.

SUMMARY

A process for the preparation of 4,5,6-trichloro-picolinic acid by the regioselective reductive dechlorination of 3,4,5,6-tetrachloropicolinic acid is provided. More particularly, the process is described for the preparation of 4,5,6-trichloropicolinic acid (Formula I)

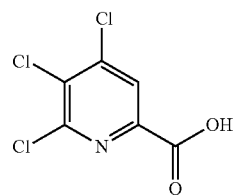

I which comprises selectively dechlorinating 3,4,5,6-tetrachloropicolinic acid (Formula II)

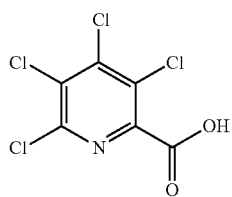

II with zinc and a catalyst prepared from a nickel compound and a bidentate ligand in a polar solvent.

Esters of 4,5,6-trichloropicolinic acid (Formula I), including unsubstituted or substituted $C_1$-$C_{12}$ alkyl esters and unsubstituted or substituted $C_7$-$C_{11}$ arylalkyl esters, can be prepared by direct esterification or transesterification reactions using techniques which are well known in the art.

DETAILED DESCRIPTION

The term "alkyl", as used herein, includes within its scope straight chain, branched chain and cyclic moieties. The term "arylalkyl", as used herein, refers to a phenyl substituted alkyl group having a total of 7 to 11 carbon atoms, such as benzyl (—$CH_2C_6H_5$), 2-methyl-naphthyl (—$CH_2C_{10}H_7$) and 1- or 2-phenethyl (—$CH_2CH_2C_6H_5$ or —$CH(CH_3)C_6H_5$).

The reductive dechlorination described herein selectively removes the 3-chloro group from 3,4,5,6-tetrachloropicolinic acid. The desired 4,5,6-trichloropicolinic acid is obtained in at least 30 percent yield. Yields up to 50 percent are possible at lower conversion rates, e.g., at 70 percent conversion.

The reducing agent is zinc, typically zinc powder (<150 microns (μm)) or zinc dust (<10 μm). While a stoichiometric amount of zinc is required, a 2- to 10-fold excess of zinc is often employed. The preferred method is to add the specified amount of zinc at the start of the reaction; however, it may also be added in portions or continuously over the course of the reaction.

The catalyst for the dechlorination is typically prepared in situ from a nickel compound and a bidentate ligand. Examples of nickel compounds are nickel(II) chloride hexahydrate [$NiCl_2.6H_2O$], anhydrous nickel(II) chloride ($NiCl_2$), (1,2-dimethoxyethane)$NiCl_2$ and (1,2-dimethoxyethane)$NiBr_2$. A preferred nickel compound is nickel(II) chloride hexahydrate [$NiCl_2.6H_2O$]. From about 2 mole percent to about 20 mole percent nickel compound is typically employed. Alternatively, the catalyst may be preformed by reaction of an appropriate nickel precursor compound, such as [$NiCl_2.6H_2O$], with a bidentate ligand. This preformed catalyst may be isolated as a solid and later employed in the reductive dechlorination reaction or the solution of preformed catalyst may be directly used for reductive dechlorination. Furthermore, the catalyst may be prepared by dissolution of the nickel compound in a polar solvent and charging the resulting solution into a solution of bidentate ligand in another polar solvent where the nickel solution could be acquired as a commercially available, aqueous solution of nickel(II) chloride.

A bidentate ligand is a ligand which can complex with a metal ion through two separate sites. Typical bidentate ligands include diamine ligands like 6,6'-dimethyl-2,2'-bipyridyl, 4,4'-dimethyl-2,2'-bipyridyl, 5-methyl-1,10-phenanthroline, 1,10-phenanthroline and 2,2'-bipyridine. The preferred bidentate ligand is 2,2'-bipyridine. From about 5 mole percent to about 40 mole percent bidentate ligand is typically employed.

The selective dechlorination is conducted in a polar solvent. Typical polar solvents are soluble in water and include acetone, acetonitrile, dimethyl sulfoxide (DMSO), ethyl alcohol, methyl alcohol, isopropyl alcohol (iPrOH), N-methylpyrrolidinone (NMP), tetrahydrofuran (THF), N,N-dimethylformamide (DMF), N,N-dimethylacetamide (DMA), hexamethylphosphoramide (HMPA) or sulfolane. Preferred polar solvents are methyl alcohol, iPrOH, THF, NMP, DMF, DMA and mixtures thereof. Most preferred are mixtures of the polar solvents with water, particularly mixtures of DMF and water. Such a reaction medium typically contains from about 75 to about 95 weight percent polar solvent and from about 5 to about 25 weight percent water. Typically the pH of the water is ≤7 although the pH may be adjusted through use of buffers or the addition of acids or bases.

The temperature at which the reaction is conducted is not critical but usually is from about 0° C. to about 85° C. and preferably from about 0° C. to about 70° C.

In a typical reaction, the nickel compound and the bidentate ligand are stirred with the polar solvent until a homogeneous solution is formed. The zinc is added as a dust or powder followed by the 3,4,5,6-tetrachloropicolinic acid. An alternative sequence of addition may be followed, such as addition of the 3,4,5,6-tetrachloropicolinic acid followed by zinc or addition of the catalyst solution to a mixture of zinc, 3,4,5,6-tetrachloropicolinic acid and solvent. Further addition sequences could be envisioned by those skilled in the art based on the restraints of a given reactor system. After completion of the reaction, solids are removed by filtration, and the filtrate is acidified. Product can be isolated by filtration or extraction with a polar organic solvent that is immiscible with water.

The following examples are presented to illustrate the processes described herein.

EXAMPLES

Example 1

Preparation of 4,5,6-trichloropicolinic Acid

Anhydrous nickel chloride (NiCl$_2$; 77 milligrams (mg), 0.596 millimoles (mmol)) and 2,2'-bipyridine (186 mg, 1.19 mmol) were stirred in 9:1 dimethylformamide (DMF)-water (10 milliliters (mL)) for 24 hours (h). Solid 3,4,5,6-tetrachloropicolinic acid (1.556 grams (g), 5.96 mmol) was added, followed by zinc powder (3.32 g, 50.7 mmol). After 3 h, water was added. The solids were removed by filtration and washed with water (100 mL). The aqueous filtrate was made acidic (pH 1) with concentrated hydrochloric acid (HCl). A white solid appeared upon standing. The solid was isolated, washed with water and dried under vacuum to give the title compound (484 mg, 35.8%) which was 94% pure by high-performance liquid chromatography (HPLC): $^1$H NMR (400 MHz, DMSO-d$_6$) δ 8.21 (s, 1H); $^{13}$C NMR (101 MHz, DMSO-d$_6$) δ 163.4, 148.9, 146.5, 144.4, 131.6, 125.7.

Example 2

Preparation of 4,5,6-trichloropicolinic Acid

In a glove box, a jar equipped with a magnetic stir bar was charged with nickel(II) chloride hexahydrate (NiCl$_2$.6H$_2$O; 119 mg, 0.500 mmol) and 2,2'-bipyridine (156 mg, 0.999 mmol). A solution of N,N-dimethylformamide (DMF) and water (9:1, 10 mL) was added and the mixture was stirred until homogenous. Zinc dust (654 mg, 10 mmol) was added. After about 10 minutes (min), solid 3,4,5,6-tetrachloropicolinic acid was added, and the mixture was stirred at ambient temperature for 20 h. The mixture was removed from the box and HCl (10 volume percent (vol %) in water; 50 mL) was added. The mixture was extracted with diethyl ether (2×25 mL). The ether extracts were combined, dried with magnesium sulfate (MgSO$_4$), filtered and concentrated in vacuo. $^1$H NMR spectroscopy in acetone-d$_6$ indicates that the major reduction product formed was 4,5,6-trichloropicolinic acid. HPLC analysis of the product mixture indicates ~70% conversion and 50% selectivity to the desired product.

Example 2b

Preparation of 4,5,6-trichloropicolinic Acid (1,2-Dimethoxyethane)NiCl$_2$ (133 mg, 0.605 mmol) and 2,2'-bipyridine (196 mg, 1.256 mmol) were stirred in 9:1 DMF-water (10 mL) under nitrogen. Within 10 min, a bright blue solution formed. Zinc powder (3.82 g, 58.4 mmol) was added followed by solid 3,4,5,6-tetrachloropicolinic acid (1.521 g, 5.83 mmol). After 3 h, the reaction mixture was filtered to remove zinc, which was washed with water (50 mL). The filtrate was diluted to 250 mL with water and then brought to pH 1 by addition of concentrated sulfuric acid which formed a gummy solid. Ethyl acetate (EtOAc; 100 mL) was added which caused the solid to dissolve. The organic layer was separated, and the aqueous layer was extracted with additional EtOAc (2×75 mL). The combined organic extracts were washed with water (5×50 mL) followed by brine, dried (MgSO$_4$) and concentrated to give a white solid (1.04 g) which had the same HPLC retention time as authentic product. HPLC analysis of the solid showed it also contained 16% starting 3,4,5,6-tetrachloropicolinic acid.

Example 3

Preparation of 4,5,6-trichloropicolinic Acid

A 25 mL scintillation vial was charged with NiCl$_2$ (76.2 mg, 0.586 mmol) and 2,2'-bipyridine (188.4 mg, 1.20 mmol). The vial was sealed and purged with nitrogen for 20 min. The inert reactor was charged with DMF (9 mL) and water (1 mL). The resulting mixture was allowed to stir for 24 h, and then solid 3,4,5,6-tetrachloropicolinic acid (1.54 g, 5.9 mmol) and zinc powder (3.33 g, 50.9 mmol) were added through the top of the reactor. The reaction mixture was allowed to stir at ambient temperature for 3 h and was diluted to 20 mL with water. The resulting heterogeneous mixture was filtered to remove the solids, and the resulting clear, aqueous filtrate was made acidic (pH~1) with concentrated HCl. Upon standing, a fine white solid formed and was collected via vacuum filtration to give the title compound (0.45 g, 33.6%) that was 86% pure as analyzed by calibrated HPLC. The residual material was 9% unreacted starting material and 2 unknown impurities.

Example 4

Preparation of 4,5,6-trichloropicolinic Acid

A 25 mL scintillation vial was charged with NiCl$_2$.6H$_2$O (84.0 mg, 0.353 mmol) and 2,2'-bipyridine (104.1 mg, 0.667 mmol). The vial was sealed and purged with nitrogen for 20 min. The inert reactor was charged with DMF (4.5 mL) and water (0.5 mL). The resulting mixture was allowed to stir for 24 h, and then solid 3,4,5,6-tetrachloropicolinic acid (0.834 g, 3.2 mmol) and zinc powder (1.6679 g, 25.5 mmol) were added through the top of the reactor. The reaction mixture was allowed to stir at ambient temperature for 3 h and was diluted to 20 mL with water. The resulting heterogeneous mixture was filtered to remove the solids, and the resulting clear, aqueous filtrate was made acidic (pH~1) using concentrated HCl. Upon standing, a fine white solid formed and was collected via vacuum filtration to give the title compound (0.25 g, 35.1%) that was 66% pure as analyzed by calibrated HPLC. The residual material was 32% unreacted starting material and several unknown low level impurities, wherein low level is less than 3.5%.

Example 5

Preparation of 4,5,6-trichloropicolinic Acid

An 8 mL scintillation vial was charged with NiCl$_2$.6H$_2$O (87.8 mg, 0.369 mmol) and 2,2'-bipyridine (119.2 mg, 0.763 mmol). The vial was closed and purged with nitrogen for 10 min, after which the vial was charged with DMF (4.5 mL) and water (0.5 mL). The mixture was allowed to stir for 5 min until a clear, bright blue solution was present. To the vial was added zinc dust (1.657 g, 25.3 mmol), and the mixture was allowed to stir under nitrogen for 35 min until a very dark blue/black solution was present. Solid 3,4,5,6-tetrachloropicolinic acid (0.831 g, 3.2 mmol) was added through the top of the reactor. The reaction mixture was allowed to stir at 27° C. for 5.5 h. The crude reaction mixture was filtered through a medium frit filter, and the filter cake was washed with DMF (2×). The resulting filtrate was diluted with an equal volume of 10% HCl (aq) to yield a clear, light yellow solution which was allowed to stir overnight at ambient temperature. The white solid was collected by vacuum filtration and was dried in an inert heating oven (50° C.; 1 h) to give the title compound (0.60 g, 83.1%) that was 69% pure as analyzed by calibrated HPLC.

Example 6

Preparation of 4,5,6-trichloropicolinic Acid

An 8 mL scintillation vial was charged with $NiCl_2 \cdot 6H_2O$ (12.5 mg, 0.053 mmol) and 2,2'-bipyridine (18.2 mg, 0.117 mmol). The vial was closed and purged with nitrogen for 5 min, after which the vial was charged with DMF (4.5 mL) and methyl alcohol ($CH_3OH$; 0.5 mL). The mixture was allowed to stir for 5 min. To the vial was added zinc dust (0.225 g, 3.4 mmol), and the mixture was allowed to stir under nitrogen for 35 min. Solid 3,4,5,6-tetrachloropicolinic acid (0.110 g, 0.4 mmol) was added through the top of the reactor. The reaction mixture was allowed to stir at 14° C. and samples were removed periodically to determine reaction kinetics. The samples (~0.01 mL of reaction mixture diluted to 1.5 mL with acetonitrile) were analyzed by a calibrated HPLC method.

TABLE 1

Weight Percent (In-Pot) of Reactant and Products as Measured by Calibrated HPLC

| Time (min) | Formula II | Formula I | 356-TCP | Residual[a] | Selectivity[b] |
|---|---|---|---|---|---|
| 0 | 100.00% | 0.00% | 0.00% | 0.00% | ND |
| 2 | 100.00% | 0.00% | 0.00% | 0.00% | ND |
| 6 | 96.16% | 3.84% | 0.00% | 0.00% | 100.00% |
| 11 | 95.03% | 4.97% | 0.00% | 0.00% | 100.00% |
| 24 | 92.27% | 6.31% | 1.42% | 0.00% | 81.61% |
| 58 | 82.70% | 14.99% | 1.39% | 0.91% | 86.67% |
| 122 | 55.76% | 39.10% | 3.36% | 1.79% | 88.37% |
| 287 | 15.24% | 76.14% | 5.25% | 3.37% | 89.83% |

356-TCP = 3,5,6-trichloropicolinic acid
[a]Residual is the sum of all other products (e.g. different regioisomers of dichloropicolinic acid (DCP)).
[b]Selectivity is calculated by [Formula I]/([Formula I] + [356-TCP] + [Residual]).
ND = not determined Example 7

Preparation of 4,5,6-trichloropicolinic Acid

An 8 mL scintillation vial was charged with $NiCl_2 \cdot 6H_2O$ (12.0 mg, 0.051 mmol) and 2,2'-bipyridine (17.0 mg, 0.109 mmol). The vial was closed and purged with nitrogen for 5 min, after which the vial was charged with DMF (4.5 mL) and isopropyl alcohol (iPrOH; 0.5 mL). The mixture was allowed to stir for 5 min. To the vial was added zinc dust (0.2194 g, 3.4 mmol), and the mixture was allowed to stir under nitrogen for 35 min. Solid 3,4,5,6-tetrachloropicolinic acid (0.1076 g, 0.4 mmol) was added through the top of the reactor. The reaction mixture was allowed to stir at 14° C. and samples were removed periodically to determine reaction kinetics. The samples (~0.01 mL of reaction mixture diluted to 1.5 mL with acetonitrile) were analyzed by a calibrated HPLC method.

TABLE 2

Weight Percent (In-Pot) of Reactant and Products as Measured by Calibrated HPLC

| Time (min) | Formula II | Formula I | 356-TCP | Residual[a] | Selectivity[b] |
|---|---|---|---|---|---|
| 0 | 100.00% | 0.00% | 0.00% | 0.00% | ND |
| 2 | 100.00% | 0.00% | 0.00% | 0.00% | ND |
| 6 | 98.42% | 1.58% | 0.00% | 0.00% | 100.00% |
| 11 | 95.93% | 4.07% | 0.00% | 0.00% | 100.00% |
| 24 | 98.33% | 1.67% | 0.00% | 0.00% | 100.00% |
| 58 | 93.32% | 6.68% | 0.00% | 0.00% | 100.00% |
| 122 | 74.45% | 24.38% | 1.18% | 0.00% | 95.39% |
| 287 | 25.51% | 63.00% | 6.41% | 5.08% | 84.57% |

356-TCP = 3,5,6-trichloropicolinic acid
[a]Residual is the sum of all other products (e.g. different regioisomers of dichloropicolinic acid (DCP)).
[b]Selectivity is calculated by [Formula I]/([Formula I] + [356-TCP] + [Residual]).
ND = not determined Example 8

Preparation of 4,5,6-trichloropicolinic Acid

Three 8 mL scintillation vials were charged with $NiCl_2 \cdot 6H_2O$ (12.0 mg, 0.051 mmol) and 2,2'-bipyridine (16.0 mg, 0.102 mmol). The vials were closed and purged with nitrogen for 5 min, after which the vials were charged with DMF (4.5 mL) and one of the following: deionized (DI) water (pH=7), 10% HCl, or 10% sodium hydroxide (NaOH) (0.5 mL). The mixtures were allowed to stir for 5 min. To each of the vials was added zinc dust (0.22 g, 3.4 mmol), and the mixtures were allowed to stir under nitrogen for 35 min. Solid 3,4,5,6-tetrachloropicolinic acid (0.10 g, 0.4 mmol) was added to each through the top of the reactor. The reaction mixtures were allowed to stir at ambient temperature, and samples were removed periodically to determine reaction kinetics. The samples (~0.01 mL of reaction mixture diluted to 1.5 mL with acetonitrile) were analyzed by a calibrated HPLC method.

TABLE 3

Weight Percent (In-Pot) of Reactant and Products as Measured by Calibrated HPLC

| Time (min) | Formula II | Formula I | 356-TCP | Residual | Selectivity |
|---|---|---|---|---|---|
| Water pH = 7 | | | | | |
| 0 | 100.00% | 0.00% | 0.00% | 0.00% | ND |
| 22 | 76.74% | 12.67% | 3.24% | 7.36% | 54.47% |
| 62 | 36.06% | 50.37% | 9.15% | 4.42% | 78.77% |
| 233 | 4.93% | 67.13% | 21.08% | 6.85% | 70.62% |
| 10% HCl | | | | | |
| 0 | 100.00% | 0.00% | 0.00% | 0.00% | ND |
| 22 | 81.69% | 10.96% | 1.65% | 5.70% | 59.85% |
| 62 | 58.28% | 28.31% | 4.92% | 8.50% | 67.85% |
| 233 | 3.78% | 71.56% | 18.85% | 5.82% | 74.37% |

TABLE 3-continued

Weight Percent (In-Pot) of Reactant and
Products as Measured by Calibrated HPLC

| Time (min) | Formula II | Formula I | 356-TCP | Residual | Selectivity |
|---|---|---|---|---|---|
| 10% NaOH | | | | | |
| 0 | 100.00% | 0.00% | 0.00% | 0.00% | ND |
| 22 | 34.88% | 0.00% | 49.63% | 15.49% | 0.00% |
| 62 | 22.18% | 0.00% | 65.88% | 11.94% | 0.00% |
| 233 | 38.47% | 0.00% | 45.11% | 16.41% | 0.00% |

356-TCP = 3,5,6-trichloropicolinic acid
[a]Residual is the sum of all other products (e.g. different regioisomers of dichloropicolinic acid (DCP)).
[b]Selectivity is calculated by [Formula I]/([Formula I] + [356-TCP] + [Residual]).
ND = not determined Example 9

Preparation of 4,5,6-trichloropicolinic Acid

Three 8 mL scintillation vials were charged with $NiCl_2 \cdot 6H_2O$ (12.0 mg, 0.051 mmol) and one of the following ligands: 6,6'-dimethyl-2,2'-bipyridyl, 4,4'-dimethyl-2,2'-bipyridyl or 5-methyl-1,10-phenanthroline (2:1 ligand/metal ratio). The vials were closed and purged with nitrogen for 5 min, after which the vials were charged with DMF (4.5 mL) and water (0.5 mL). The mixtures were allowed to stir for 5 min. To each of the vials was added zinc dust (0.22 g, 3.4 mmol), and the mixtures were allowed to stir under nitrogen for 35 min. Solid 3,4,5,6-tetrachloropicolinic acid (0.10 g, 0.4 mmol) was added to each through the top of the reactor. The reaction mixtures were allowed to stir at ambient temperature, and samples were removed periodically to determine reaction kinetics. The samples (~0.01 mL of reaction mixture diluted to 1.5 mL with acetonitrile) were analyzed by a calibrated HPLC method.

TABLE 4

Weight Percent (In-Pot) of Reactant and
Products as Measured by Calibrated HPLC

| Time (min) | Formula II | Formula I | 356-TCP | Residual | Selectivity |
|---|---|---|---|---|---|
| 6,6'-Dimethyl-2,2'-bipyridyl | | | | | |
| 0 | 100.00% | 0.00% | 0.00% | 0.00% | ND |
| 2 | 88.61% | 7.04% | 0.00% | 4.35% | 61.81% |
| 6 | 87.11% | 10.49% | 0.00% | 2.40% | 81.39% |
| 11 | 85.73% | 12.19% | 0.00% | 2.07% | 85.46% |
| 24 | 78.95% | 14.81% | 2.25% | 3.99% | 70.34% |
| 58 | 68.26% | 20.81% | 4.07% | 6.86% | 65.55% |
| 122 | 52.54% | 28.31% | 9.38% | 9.76% | 59.65% |
| 287 | 44.23% | 32.71% | 12.49% | 10.57% | 58.65% |
| 4,4'-Dimethyl-2,2'-bipyridyl | | | | | |
| 0 | 100.00% | 0.00% | 0.00% | 0.00% | ND |
| 2 | 98.26% | 1.74% | 0.00% | 0.00% | 100.00% |
| 6 | 97.91% | 0.73% | 0.88% | 0.48% | 35.06% |
| 11 | 93.95% | 0.74% | 3.16% | 2.16% | 12.17% |
| 24 | 89.16% | 2.13% | 5.63% | 3.08% | 19.66% |
| 58 | 76.94% | 4.41% | 5.11% | 13.53% | 19.14% |
| 122 | 62.95% | 14.86% | 10.24% | 11.94% | 40.12% |
| 287 | 34.00% | 35.59% | 18.48% | 11.93% | 53.92% |
| 5-Methyl-1,10-phenanthroline | | | | | |
| 0 | 100.00% | 0.00% | 0.00% | 0.00% | ND |
| 2 | 100.00% | 0.00% | 0.00% | 0.00% | ND |
| 6 | 98.96% | 1.04% | 0.00% | 0.00% | 100.00% |
| 11 | 94.30% | 4.69% | 0.00% | 1.01% | 82.22% |
| 24 | 89.66% | 7.96% | 0.00% | 2.37% | 77.06% |
| 58 | 70.93% | 15.44% | 0.00% | 13.63% | 53.10% |
| 122 | 46.51% | 46.74% | 0.00% | 6.75% | 87.39% |
| 287 | 30.94% | 60.29% | 0.00% | 8.78% | 87.29% |

356-TCP = 3,5,6-trichloropicolinic acid
[a]Residual is the sum of all other products (e.g. different regioisomers of dichloropicolinic acid (DCP)).
[b]Selectivity is calculated by [Formula I]/([Formula I] + [356-TCP] + [Residual]).
ND = not determined Example 10

Preparation of 4,5,6-trichloropicolinic Acid

Four 8 mL scintillation vials were charged with $NiCl_2 \cdot 6H_2O$ (12.0 mg, 0.051 mmol) and 2,2'-bipyridine (16.0 mg, 0.102 mmol). The vials were closed and purged with nitrogen for 5 min, after which the vials were charged with one of the following solvents: acetonitrile, acetone, methyl alcohol, or tetrahydrofuran (4.5 mL) and water (0.5 mL). The mixtures were allowed to stir for 5 min. To each of the vials was added zinc dust (0.22 g, 3.4 mmol), and the mixtures were allowed to stir under nitrogen for 35 min. Solid 3,4,5,6-tetrachloropicolinic acid (0.10 g, 0.4 mmol) was added to each through the top of the reactor. The reaction mixtures were allowed to stir at ambient temperature, and samples were removed periodically to determine reaction kinetics. The samples (~0.01 mL of reaction mixture diluted to 1.5 mL with acetonitrile) were analyzed by a calibrated HPLC method.

TABLE 5

Weight Percent (In-Pot) of Formula
I as Measured by Calibrated HPLC

| | Formula I | |
|---|---|---|
| Solvent | 141 min | 286 min |
| Methyl alcohol | 31.12% | 53.58% |
| Acetone | 41.35% | 53.07% |
| Acetonitrile | 26.15% | 40.65% |
| Tetrahydrofuran | 80.87% | 61.96% |

Example 11

Preparation of 4,5,6-trichloropicolinic Acid

A 100 mL round bottom flask equipped with a magnetic stir bar was charged with $NiCl_2 \cdot 6H_2O$ (105 mg, 0.442 mmol), 2,2'-bipyridine (150 mg, 0.960 mmol), DMF (15 mL) and water (2 mL). The resulting mixture was allowed to stir for 5 min, and then zinc dust (2.006 g, 30.7 mmol) was added. The reaction mixture was allowed to stir at ambient temperature for 15 min until a very dark blue/black solution was present. Solid 3,4,5,6-tetrachloropicolinic acid (2.017 g, 7.7 mmol) was added through the top of the reactor. The reaction mixture was allowed to stir at 27° C. for 5.25 h, and the crude reaction mixture was filtered through a course frit filter and washed with DMF (5 mL). The resulting filtrate was diluted with an equal volume of 10% HCl (aq) which resulted in the precipitation of a light yellow solid that was collected by filtration. The solid was collected by vacuum filtration to give the title compound (2.32 g, 81.5%) that was 61.5% pure as analyzed by calibrated HPLC.

Calibrated HPLC Method

Sample/Standard Preparation: A 20 milliliter scintillation vial was charged with substrate/standard (~20 mg) and propiophenone (Sigma-Aldrich, 99%; ISTD, 20 mg). The mixture was dissolved in acetonitrile (HPLC Grade, Fisher Scientific; 10 mL). If necessary, ultrasonication was used to help dissolution. An aliquot of the solution (~0.5 mL) was diluted to 1.5 mL with acetonitrile as the diluent. The resulting solution was analyzed by HPLC. Identification and quantification were achieved by comparing peak retention times and areas with those from standard compounds and mixtures.

HPLC Conditions:

| Column | Agilent Poroshell 120 Phenylhexyl, 2.7 micron (μm), 4.6 × 150 millimeters (mm; P/N: 693975-912) | | | | |
|---|---|---|---|---|---|
| Solvents | A: water (0.1% formic acid) B: acetonitrile (0.1% formic acid) | | | | |
| Gradient Program | Time (min): | 0 | 30 | 30.1 | 35 |
| | % Solvent B: | 20 | 90 | 20 | 20 |
| Column flow rate | 1.0 mL/min | | | | |
| Injection Volume | 2.0 microliters (μL) | | | | |
| Temperature | 35° C. | | | | |
| Detector wavelength | 236 nanometers (nm) | | | | |

Retention Times for Standards:

| Substrate/Standard | Retention Time (min) |
|---|---|
| Propiophenone (ISTD) | 10.94 |
| 4,5,6-Trichloropicolinic Acid (Formula I) | 9.36 |
| 3,4,5,6-Tetrachloropicolinic Acid (Formula II) | 8.32 |
| 3,5,6-Trichloropicolinic Acid (356-TCP) | 6.35 |

Response Factor for Substrate:

$$\text{Response Factor} = \frac{(LC \text{ Area for Substrate} * \text{Mass of } ISTD)}{(LC \text{ Area for } ISTD * \text{Mass of Substrate})}$$

Mass of Substrate:

$$\text{Mass of Substrate} = \frac{(LC \text{ Area for Substrate} * \text{mass of } ISTD)}{(LC \text{ Area for } ISTD * \text{Response Factor for Substrate})}$$

Purity of Substrate:

$$\text{Purity of Substrate} = \frac{\text{Mass of Substrate}}{\text{Mass of Isolated Solid}}$$

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A process for the preparation of 4,5,6-trichloropicolinic acid (Formula I)

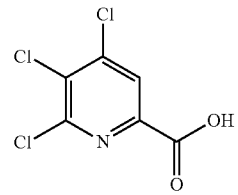

which comprises, selectively dechlorinating 3,4,5,6-tetrachloropicolinic acid (Formula II)

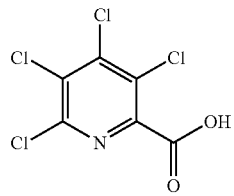

with zinc and a catalyst prepared from a nickel compound and a bidentate ligand in a polar solvent.

2. The process of claim 1, wherein the nickel compound is NiCl$_2$.6H$_2$O.

3. The process of claim 1, wherein the polar solvent is acetone, acetonitrile, dimethyl sulfoxide (DMSO), ethyl alcohol, methyl alcohol, isopropyl alcohol (iPrOH), N-methylpyrrolidinone (NMP), tetrahydrofuran (THF), N,N-dimethyl-formamide (DMF), N,N-dimethylacetamide (DMA), hexamethylphosphoramide (HMPA) or sulfolane.

4. The process of claim 3, wherein the polar solvent is methyl alcohol, ethyl alcohol, iPrOH, THF, NMP, DMF, DMA or mixtures thereof.

5. The process of claim 3 or 4, wherein the polar solvent is a mixture of the polar solvent with water.

6. The process of claim 4, wherein the polar solvent is N,N-dimethylformamide.

7. The process of claim 5, wherein the aqueous polar solvent is a mixture from about 75 to about 95 weight percent polar solvent and from about 5 to about 25 weight percent water.

8. The process of claim 1, wherein the bidentate ligand is 6,6'-dimethyl-2,2'-bipyridyl, 4,4'-dimethyl-2,2'-bipyridyl, 5-methyl-1,10-phenanthroline, 1,10-phenanthroline or 2,2'-bipyridine.

9. The process of claim 8, wherein the bidentate ligand is 2,2'-bipyridine.

10. The process of claim 1, wherein the zinc is zinc powder or zinc dust.

11. The process of claim 1, wherein the pH of the solution is neutral or acidic.

12. The process of claim 10, wherein the zinc powder is <150 μm.

13. The process of claim 10, wherein the zinc dust is <10 μm.

* * * * *